United States Patent
Miyake et al.

(10) Patent No.: US 11,203,644 B2
(45) Date of Patent: Dec. 21, 2021

(54) ANTI-TLR9 ANTIBODY, PHARMACEUTICAL COMPOSITION, AND KIT

(71) Applicant: The University of Tokyo, Tokyo (JP)

(72) Inventors: Kensuke Miyake, Tokyo (JP); Yusuke Murakami, Tokyo (JP); Ryutaro Fukui, Tokyo (JP)

(73) Assignee: The University of Tokyo, Tokyo (JP)

( * ) Notice: Subject to any disclaimer, the term of this patent is extended or adjusted under 35 U.S.C. 154(b) by 11 days.

(21) Appl. No.: 16/465,833

(22) PCT Filed: Nov. 30, 2017

(86) PCT No.: PCT/JP2017/043124
§ 371 (c)(1),
(2) Date: May 31, 2019

(87) PCT Pub. No.: WO2018/101425
PCT Pub. Date: Jun. 7, 2018

(65) Prior Publication Data
US 2019/0292270 A1    Sep. 26, 2019

(30) Foreign Application Priority Data

Dec. 2, 2016 (JP) .................. JP2016-235262

(51) Int. Cl.
*C07K 16/28* (2006.01)
*A61K 39/395* (2006.01)
*A61P 37/06* (2006.01)
*G01N 33/563* (2006.01)
*C12N 15/09* (2006.01)
*A61P 17/06* (2006.01)
*A61P 1/16* (2006.01)

(52) U.S. Cl.
CPC ........ *C07K 16/2896* (2013.01); *A61K 39/395* (2013.01); *C07K 16/28* (2013.01); *A61P 1/16* (2018.01); *A61P 17/06* (2018.01); *A61P 37/06* (2018.01); *C07K 2317/24* (2013.01); *C12N 15/09* (2013.01); *G01N 33/563* (2013.01)

(58) Field of Classification Search
None
See application file for complete search history.

(56) References Cited

U.S. PATENT DOCUMENTS

2005/0244410 A1* 11/2005 Bassiri ............... C07K 16/2896
                                                        424/144.1
2010/0291577 A1* 11/2010 Latz .................. G01N 33/5041
                                                        435/6.16
2016/0185871 A1   6/2016 Miyake et al.

FOREIGN PATENT DOCUMENTS

WO        2014174704 A    10/2014

OTHER PUBLICATIONS

Antibody eB72-1665 eBioscience Datasheet, ThermoFisher Cataolog #12-9099-82, Datasheet retrieved from: <URL: https://www.thermofisher.com/order/genome-database/dataSheetPdf?producttype=antibody&productsubtype=antibody_primary&productId=12-9099-82&version=114>. [retrieved on Aug. 28, 2020]), 2020.*

(Continued)

*Primary Examiner* — Claire Kaufman
(74) *Attorney, Agent, or Firm* — Suzannah K Sundby, Esq.; Canady + Lortz LLP

(57) ABSTRACT

The present invention provides a novel antibody targeting TLR9.

19 Claims, 3 Drawing Sheets

Specification includes a Sequence Listing.

(56) References Cited

OTHER PUBLICATIONS

EMBL-EBI Training Glossary, "N-terminus", retrieved online from <URL:https://www.ebi.ac.uk/training/online/glossary/n-terminus>, retrieved on Dec. 22, 2020, 2020.*

Murakami et al., The protective effect of the anti-Toll-like receptor 9 antibody against acute cytokine storm caused by immunostimulatory DNA, Sci. Reports, 7:44042, Mar. 7, 2017.*

Tripathi et al., ATLR9 agonist promotes IL-22-dependent pancreatic islet allograft survival in type 1 diabetic mice, Nat. Commun. 7: 13896 (pp. 1-14), Dec. 16, 2016.*

Suthers et al., Blood (2017) 130 (Supplement 1): 75, Dec. 7, 2017.*

Anti-TLR9 antibody,clone NaR9, Millipore Sigma, retrieved from : <URL: https://www.emdmillipore.com/US/en/product/Anti-TLR9-Antibody-clone-NaR9,MM_NF-MABF2156-25UL>, retrived on Aug. 28, 2020.*

Fukui et al., New application of anti-TLR monoclonal antibodies: detection, inhibition and protection, Inflam. Regeneration, 38:11, 2018.*

International Search Report received in PCT/JP2017/043124 dated Feb. 27, 2018.

Written Opinion received in PCT/JP2017/043124 dated Feb. 27, 2018.

Barton, et al., "Intracellular localization of Toll-like receptor 9 prevents recognition of self DNA but facilitates access to viral DNA", Dec. 11, 2005, pp. 49-56, vol. 7, No. 1, Publisher: Nature Immunology.

Ewald, et al., "The ectodomain of Toll-like receptor 9 is cleaved to generate a functional receptor", Dec. 4, 2008, pp. 658-662, vol. 456, No. 7222, Publisher: Nature.

Lande, et al., "Plasmacytoid dendritic cells sense self-DNA coupled with antimicrobial peptide", Oct. 4, 2007, pp. 564-569, vol. 449, No. 7162, Publisher: Nature.

Murakami, et al., "Targeting cell surface Toll-like receptor 9 to control innate immune responses", Nov. 24, 2016, pp. 143 (3-B-W24-12-P), vol. 45, Publisher: Proceedings of the Japanese Society for Immunology.

* cited by examiner

Mouse TLR9/Human TLR9 chimera staining with NaR9

Figure 8

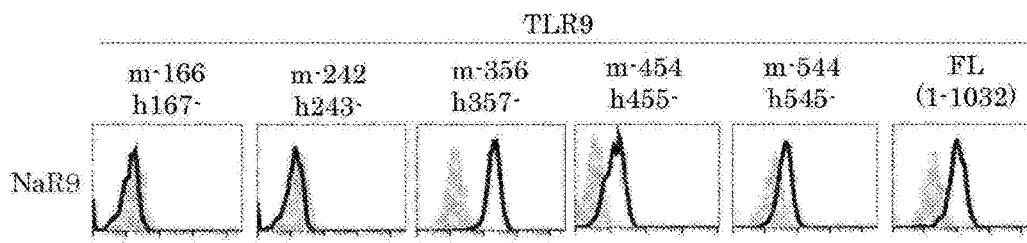

Figure 9 Heavy chain: Amino acids sequence (135 aa)

Leader sequence-FR1-CDR1-FR2-CDR2-FR3-CDR3-FR4

MRWSWIFLFLLSITAGVHCQVQLQQSGPDLVKPGASVQMSCKTSGYTFTNYYLHWVKQRPGQGLEWI
GWIYPGDGSTKYNDQFRGRFTLTADKSSSTAYMFLSRLTSEDSAIYFCAKSWDYFDYWGQGTTLTVS
S

Figure 10 Heavy chain: DNA sequence (405 bp)

Leader sequence-FR1-CDR1-FR2-CDR2-FR3-CDR3-FR4

ATGCGATGGAGCTGGATCTTTCTCTTCCTCCTGTCAATAACTGCAGGTGTCCATTGCCAGGTCCAGC
TGCAGCAGTCTGGACCTGACCTGGTGAAGCCTGGGGCTTCAGTGAAGATGTCCTGCAAGACTTCTGG
CTACACCTTCACAAACTACTATTTACACTGGGTGAAGCAGAGGCCTGGACAGGGACTTGAGTGGATT
GGATGGATTTATCCTGGAGATGGTAGCACTAAGTACAATGACCAGTTCAGGGGCAGGACCACACTGA
CTGCAGACAAATCCTCCAGCACAGCCTACATGTTCCTCAGCAGCCTGACCTCTGAGGACTCTGCCAT
CTATTTCTGTGCCAAGAGCTGGGACTATTTTGACTACTGGGGCCAAGGCACCACTCTCACAGTCTCC
TCA

Figure 11 Light chain: Amino acids sequence (126 aa)

Leader sequence-FR1-CDR1-FR2-CDR2-FR3-CDR3-FR4

MRPSIQFLGLLLFWLHGAQCDIQMTQSPSSLSASLGERVTITCKASQDIDNYIAWYQHKPGKGPRLL
IHYASTLQPGIPSRFSGSGSGRDYSLTISNLEPEDIATYYCLQYDDLYTFGGGTKLEIK

Figure 12 Light chain: DNA sequence (378 bp)

Leader sequence-FR1-CDR1-FR2-CDR2-FR3-CDR3-FR4

ATGAGACCGTCTATTCAGTTCCTGGGGCTCTTGTTGTTCTGGCTTCATGGTGCTCAGTGTGACATCC
AGATGACACAGTCTCCATCCTCACTGTCTGCATCTCTGGGAGGCAGAGTCACCATCACTTGCAAGGC
AAGCCAAGACATTGACAATTATATAGCTTGGTACCAGCACAAGCCTGGAAAAGGTCCTAGGCTACTC
ATACATTACGCATCTACATTACAGCCGGGCATCCCATCAAGGTTCAGTGGAAGTGGGTCTGGGAGAC
ATTATTCCTCAGCATCAGCAACCTGGAACCTGAAGATATTGCAACTTATTATTGTCTACAGTATGA
TGATCTATATACGTTCGGAGGGGGGACCAAGCTGGAAATAAAA

```
                        SEQUENCE LISTING

<160> NUMBER OF SEQ ID NOS: 20

<210> SEQ ID NO 1
<211> LENGTH: 1032
<212> TYPE: PRT
<213> ORGANISM: Mus musculus

<400> SEQUENCE: 1

Met Val Leu Arg Arg Arg Thr Leu His Pro Leu Ser Leu Leu Val Gln
1               5                   10                  15

Ala Ala Val Leu Ala Glu Thr Leu Ala Leu Gly Thr Leu Pro Ala Phe
                20                  25                  30

Leu Pro Cys Glu Leu Lys Pro His Gly Leu Val Asp Cys Asn Trp Leu
            35                  40                  45

Phe Leu Lys Ser Val Pro Arg Phe Ser Ala Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
        115                 120                 125

Asn Leu Ser Tyr Asn Gly Ile Thr Thr Val Pro Arg Leu Pro Ser Ser
    130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
        195                 200                 205

Asn Asn Leu Thr Lys Val Pro Arg Gln Leu Pro Pro Ser Leu Glu Tyr
```

```
                210                 215                 220
Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
                260                 265                 270

Leu His Leu His Pro Glu Thr Phe His His Leu Ser His Leu Glu Gly
                275                 280                 285

Leu Val Leu Lys Asp Ser Ser Leu His Thr Leu Asn Ser Ser Trp Phe
                290                 295                 300

Gln Gly Leu Val Asn Leu Ser Val Leu Asp Leu Ser Glu Asn Phe Leu
305                 310                 315                 320

Tyr Glu Ser Ile Thr His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
                340                 345                 350

Arg Leu His Leu Ala Ser Ser Phe Lys Asn Leu Val Ser Leu Gln Glu
                355                 360                 365

Leu Asn Met Asn Gly Ile Phe Phe Arg Leu Leu Asn Lys Tyr Thr Leu
                370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
                420                 425                 430

Leu Ser Glu Ala Thr Pro Glu Glu Ala Asp Asp Ala Glu Gln Glu Glu
                435                 440                 445

Leu Leu Ser Ala Asp Pro His Pro Ala Pro Leu Ser Thr Pro Ala Ser
                450                 455                 460

Lys Asn Phe Met Asp Arg Cys Lys Asn Phe Lys Phe Thr Met Asp Leu
465                 470                 475                 480

Ser Arg Asn Asn Leu Val Thr Ile Lys Pro Glu Met Phe Val Asn Leu
                485                 490                 495

Ser Arg Leu Gln Cys Leu Ser Leu Ser His Asn Ser Ile Ala Gln Ala
                500                 505                 510

Val Asn Gly Ser Gln Phe Leu Pro Leu Thr Asn Leu Gln Val Leu Asp
                515                 520                 525

Leu Ser His Asn Lys Leu Asp Leu Tyr His Trp Lys Ser Phe Ser Glu
                530                 535                 540

Leu Pro Gln Leu Gln Ala Leu Asp Leu Ser Tyr Asn Ser Gln Pro Phe
545                 550                 555                 560

Ser Met Lys Gly Ile Gly His Asn Phe Ser Phe Val Thr His Leu Ser
                565                 570                 575

Met Leu Gln Ser Leu Ser Leu Ala His Asn Asp Ile His Thr Arg Val
                580                 585                 590

Ser Ser His Leu Asn Ser Asn Ser Val Arg Phe Leu Asp Phe Ser Gly
                595                 600                 605

Asn Gly Met Gly Arg Met Trp Asp Glu Gly Gly Leu Tyr Leu His Phe
                610                 615                 620

Phe Gln Gly Leu Ser Gly Leu Leu Lys Leu Asp Leu Ser Gln Asn Asn
625                 630                 635                 640
```

```
Leu His Ile Leu Arg Pro Gln Asn Leu Asp Asn Leu Pro Lys Ser Leu
                645                 650                 655

Lys Leu Leu Ser Leu Arg Asp Asn Tyr Leu Ser Phe Phe Asn Trp Thr
            660                 665                 670

Ser Leu Ser Phe Leu Pro Asn Leu Glu Val Leu Asp Leu Ala Gly Asn
        675                 680                 685

Gln Leu Lys Ala Leu Thr Asn Gly Thr Leu Pro Asn Gly Thr Leu Leu
    690                 695                 700

Gln Lys Leu Asp Val Ser Ser Asn Ser Ile Val Ser Val Val Pro Ala
705                 710                 715                 720

Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
            740                 745                 750

Leu Thr Val Leu Asp Val Arg Ser Asn Pro Leu His Cys Ala Cys Gly
        755                 760                 765

Ala Ala Phe Val Asp Leu Leu Leu Glu Val Gln Thr Lys Val Pro Gly
    770                 775                 780

Leu Ala Asn Gly Val Lys Cys Gly Ser Pro Gly Gln Leu Gln Gly Arg
785                 790                 795                 800

Ser Ile Phe Ala Gln Asp Leu Arg Leu Cys Leu Asp Glu Val Leu Ser
                805                 810                 815

Trp Asp Cys Phe Gly Leu Ser Leu Leu Ala Val Ala Val Gly Met Val
            820                 825                 830

Val Pro Ile Leu His His Leu Cys Gly Trp Asp Val Trp Tyr Cys Phe
        835                 840                 845

His Leu Cys Leu Ala Trp Leu Pro Leu Leu Ala Arg Ser Arg Arg Ser
    850                 855                 860

Ala Gln Thr Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
            900                 905                 910

Trp Leu Pro Gly Gln Thr Leu Phe Glu Asn Leu Trp Ala Ser Ile Tyr
        915                 920                 925

Gly Ser Arg Lys Thr Leu Phe Val Leu Ala His Thr Asp Arg Val Ser
    930                 935                 940

Gly Leu Leu Arg Thr Ser Phe Leu Leu Ala Gln Gln Arg Leu Leu Glu
945                 950                 955                 960

Asp Arg Lys Asp Val Val Val Leu Val Ile Leu Arg Pro Asp Ala His
                965                 970                 975

Arg Ser Arg Tyr Val Arg Leu Arg Gln Arg Leu Cys Arg Gln Ser Val
            980                 985                 990

Leu Phe Trp Pro Gln Gln Pro Asn Gly Gln Gly Gly Phe Trp Ala Gln
        995                 1000                1005

Leu Ser Thr Ala Leu Thr Arg Asp Asn Arg His Phe Tyr Asn Gln
    1010                1015                1020

Asn Phe Cys Arg Gly Pro Thr Ala Glu
    1025                1030

<210> SEQ ID NO 2
<211> LENGTH: 5
```

```
<212> TYPE: PRT
<213> ORGANISM: Mus musculus

<400> SEQUENCE: 2

Asn Tyr Tyr Leu His
1               5

<210> SEQ ID NO 3
<211> LENGTH: 15
<212> TYPE: DNA
<213> ORGANISM: Mus musculus

<400> SEQUENCE: 3
aactactatt tacac                                                    15

<210> SEQ ID NO 4
<211> LENGTH: 17
<212> TYPE: PRT
<213> ORGANISM: Mus musculus

<400> SEQUENCE: 4

Trp Ile Tyr Pro Gly Asp Gly Ser Thr Lys Tyr Asn Asp Gln Phe Arg
1               5                   10                  15

Gly

<210> SEQ ID NO 5
<211> LENGTH: 51
<212> TYPE: DNA
<213> ORGANISM: Mus musculus

<400> SEQUENCE: 5
tggatttatc ctggagatgg tagcactaag tacaatgacc agttcagggg c             51

<210> SEQ ID NO 6
<211> LENGTH: 7
<212> TYPE: PRT
<213> ORGANISM: Mus musculus

<400> SEQUENCE: 6

Ser Trp Asp Tyr Phe Asp Tyr
1               5

<210> SEQ ID NO 7
<211> LENGTH: 21
<212> TYPE: DNA
<213> ORGANISM: Mus musculus

<400> SEQUENCE: 7
agctgggact attttgacta c                                             21

<210> SEQ ID NO 8
<211> LENGTH: 11
<212> TYPE: PRT
<213> ORGANISM: Mus musculus

<400> SEQUENCE: 8

Lys Ala Ser Gln Asp Ile Asp Asn Tyr Ile Ala
1               5                   10

<210> SEQ ID NO 9
<211> LENGTH: 33
<212> TYPE: DNA
<213> ORGANISM: Mus musculus
```

<400> SEQUENCE: 9
aaggcaagcc aagacattga caattatata gct                                33

<210> SEQ ID NO 10
<211> LENGTH: 7
<212> TYPE: PRT
<213> ORGANISM: Mus musculus

<400> SEQUENCE: 10

Tyr Ala Ser Thr Leu Gln Pro
1               5

<210> SEQ ID NO 11
<211> LENGTH: 21
<212> TYPE: DNA
<213> ORGANISM: Mus musculus

<400> SEQUENCE: 11
tacgcatcta cattacagcc g                                             21

<210> SEQ ID NO 12
<211> LENGTH: 8
<212> TYPE: PRT
<213> ORGANISM: Mus musculus

<400> SEQUENCE: 12

Leu Gln Tyr Asp Asp Leu Tyr Thr
1               5

<210> SEQ ID NO 13
<211> LENGTH: 24
<212> TYPE: DNA
<213> ORGANISM: Mus musculus

<400> SEQUENCE: 13
ctacagtatg atgatctata tacg                                          24

<210> SEQ ID NO 14
<211> LENGTH: 135
<212> TYPE: PRT
<213> ORGANISM: Mus musculus

<400> SEQUENCE: 14

Met Arg Trp Ser Trp Ile Phe Leu Phe Leu Leu Ser Ile Thr Ala Gly
1               5                   10                  15

Val His Cys Gln Val His Leu Gln Gln Ser Gly Pro Asp Leu Val Lys
            20                  25                  30

Pro Gly Ala Ser Val Gln Met Ser Cys Lys Thr Ser Asp Tyr Thr Phe
        35                  40                  45

Thr Asn Tyr Tyr Leu His Trp Val Arg Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Asp Gln Phe Arg Gly Arg Thr Thr Leu Thr Ala Asp Lys Ser Ser Ser
                85                  90                  95

Thr Ala Tyr Met Phe Leu Ser Ser Leu Thr Ser Glu Asp Ser Ala Ile
            100                 105                 110

Tyr Phe Cys Ala Lys Ser Trp Asp Tyr Phe Asp Tyr Trp Gly Gln Gly
        115                 120                 125

Thr Thr Leu Thr Val Ser Ser

<210> SEQ ID NO 15
<211> LENGTH: 405
<212> TYPE: DNA
<213> ORGANISM: Mus musculus

<400> SEQUENCE: 15

```
atgcgatgga gctggatctt tctcttcctc ctgtcaataa ctgcaggtgt ccattgccag    60
gtccatctgc agcagtctgg acctgacctg gtgaagcctg ggcttcagt gcagatgtcc   120
tgcaagactt ctgactacac cttcacaaac tactatttac actgggtgag gcagaggcct   180
ggacagggac ttgagtggat tggatggatt tatcctggag atggtagcac taagtacaat   240
gaccagttca gggcaggac cacactgact gcagacaaat cctccagcac agcctacatg   300
ttcctcagca gcctgacctc tgaggactct gcgatctatt tctgtgcgaa gagctgggac   360
tattttgact actggggcca aggcaccact ctcacagtct cctca               405
```

<210> SEQ ID NO 16
<211> LENGTH: 126
<212> TYPE: PRT
<213> ORGANISM: Mus musculus

<400> SEQUENCE: 16

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asp Asn Tyr Ile Ala Trp Tyr Gln His Lys Pro Gly Lys Gly Pro
    50                  55                  60

Arg Leu Leu Ile His Tyr Ala Ser Thr Leu Gln Pro Gly Ile Pro Ser
65                  70                  75                  80

Arg Phe Ser Gly Ser Gly Ser Gly Arg Asp Tyr Ser Leu Ser Ile Ser
                85                  90                  95

Asn Leu Glu Pro Glu Asp Ile Ala Thr Tyr Tyr Cys Leu Gln Tyr Asp
            100                 105                 110

Asp Leu Tyr Thr Phe Gly Gly Gly Thr Lys Leu Glu Ile Lys
        115                 120                 125
```

<210> SEQ ID NO 17
<211> LENGTH: 378
<212> TYPE: DNA
<213> ORGANISM: Mus musculus

<400> SEQUENCE: 17

```
atgagaccgt ctattcagtt cctggggctc ttgttgttct ggcttcatgg tgctcagtgt    60
gacatccaga tgacacagtc tccatcctca ctgtctgcat ctctgggagg caaagtcacc   120
atcacttgca aggcaagcca agacattgac aattatatag cttggtacca gcacaagcct   180
ggaaaaggtc ctaggctact catacattac gcatctacat tacagccggg catcccatca   240
aggttcagtg gaagtgggtc tgggagagat tattccctca gcatcagcaa cctggaacct   300
gaagatattg caacttatta ttgtctacag tatgatgatc tatatacgtt cggagggggg   360
accaagctgg aaataaaa                                                378
```

```
<210> SEQ ID NO 18
<211> LENGTH: 20
<212> TYPE: DNA
<213> ORGANISM: Artificial Sequence
<220> FEATURE:
<223> OTHER INFORMATION: CpGB 1688
<220> FEATURE:
<221> NAME/KEY: misc_feature
<222> LOCATION: (1)..(20)
<223> OTHER INFORMATION: phosphorothioate

<400> SEQUENCE: 18
tccatgacgt tcctgatgct                                                   20

<210> SEQ ID NO 19
<211> LENGTH: 20
<212> TYPE: DNA
<213> ORGANISM: Artificial Sequence
<220> FEATURE:
<223> OTHER INFORMATION: CpGA 1585
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (15)..(19)
<223> OTHER INFORMATION: phosphorothioate

<400> SEQUENCE: 19
ggggtcaacg ttgagggggg                                                   20

<210> SEQ ID NO 20
<211> LENGTH: 19
<212> TYPE: RNA
<213> ORGANISM: Artificial Sequence
<220> FEATURE:
<223> OTHER INFORMATION: Poly U
<220> FEATURE:
<221> NAME/KEY: misc_feature
<222> LOCATION: (1)..(19)
<223> OTHER INFORMATION: phosphorothioate

<400> SEQUENCE: 20
uuuuuuuuuu uuuuuuuuu                                                    19
```

ANTI-TLR9 ANTIBODY, PHARMACEUTICAL COMPOSITION, AND KIT

TECHNICAL FIELD

The present invention relates to an anti-TLR9 antibody, a pharmaceutical composition and a kit.

BACKGROUND ART

Toll-like receptors (TLRs) form a family of pathogen sensors. TLRs induce various activation signals and phylactic responses by recognizing specific pathogen components. TLRs are not only important for a defense against infection but also involved in autoimmune inflammatory diseases and the like.

Of approximately 10 types of TLRs, TLR3, TLR7, TLR8, and TLR9 are distributed in endoplasmic reticula which are intracellular organelles and recognize bacterium- or virus-derived nucleic acids. TLR7 and TLR8 recognize single-stranded RNA, while TLR9 recognizes unmethylated single-stranded DNA containing CpG motifs (CpG-DNA). However, unlike double-stranded RNA specific for viruses, single-stranded RNA or DNA does not greatly differ from a nucleic acid derived from host cells. Thus, TLRs cause a response against own cells, leading to autoimmune diseases, without precise control of their ligand recognition mechanism.

In this respect, the autoimmune response caused by TLR9 is controlled by limiting a nucleic acid recognition site to endolysosome (Non Patent Literature 1). In a steady state, extracellular self-nucleic acids are rapidly degraded so that the nucleic acids do not reach intracellular endolysosome and therefore, are not recognized by TLR9. On the other hand, microbial nucleic acids are protected by bacterial cell walls or virions and therefore reach endolysosome where the nucleic acids are released for the first time and recognized by TLR9.

By contrast, self-nucleic acids acquire resistance to degradation through interaction with an antimicrobial peptide or an autoantibody and can thereby reach endolysosome. As the result, TLR9-dependent autoimmune responses are caused. In fact, the relation of TLR9 to psoriasis or systemic lupus erythematosus (SLE) has been suggested (Non Patent Literature 2).

TLR9 is therefore thought to be a therapeutic target in TLR9-dependent autoimmune diseases such as psoriasis and SLE. Various methods for suppressing the expression or function of TLR9 have hitherto been proposed. Specifically, a method using oligo DNA having an antagonism against TLR9, microRNA suppressing the expression of TLR9, or the like has been attempted. In general, however, the safety of nucleic acid drugs is unknown. In addition, it cannot be denied that the complete suppression of the function of TLR9 may cause a risk such as infectious diseases.

From the standpoint of safety and specificity, antibody drugs are desired. As described above, however, TLR9 is localized in endolysosome and isolated from the cell surface in order to limit an autoimmune response, probably hindering use of antibodies acting only on the cell surface. As a result, there have been few attempts to use an antibody drug against TLR9.

It has been reported that the cleavage of the extracellular domain of TLR9 by a kind of proteinase, such as cathepsin family, in endolysosome is necessary for exerting the function of TLR9 (Non Patent Literature 3). In other words, mainly the C-terminal side of TLR9 has been thought to be important for exerting the function of TLR9.

CITATION LIST

Non Patent Literature

Non Patent Literature 1: Barton, G. et al., d Medzhitov, R. Nat Immunol 7, 49-56. (2006)
Non Patent Literature 2: Lande, R. et al., Nature 449, 564-569 (2007)
Non Patent Literature 3: Ewald, S. E. et al., The ectodomain of Toll-like receptor 9 is cleaved to generate a functional receptor. Nature 456, 658-662 (2008)

SUMMARY OF INVENTION

Technical Problem

An object of the present invention is to provide a novel antibody targeting TLR9.

Solution to Problem

The present inventors have conducted diligent studies to attain the object and consequently completed the present invention by finding that, surprisingly, an antibody recognizing the N terminus which is an extracellular region to be cleaved from TLR9 has a TLR9 response suppressive effect.

Specifically, the invention of the present application encompasses the following aspects.

[1] An antibody recognizing the N terminus of TLR9.
[2] The antibody according to [1], wherein the antibody recognizes a region from positions 1 to 356 at the N terminus of TLR9.
[3] The antibody according to [1] or [2], wherein the antibody recognizes a region from positions 243 to 356 at the N terminus of TLR9.
[4] The antibody according to any of [1] to [3], wherein the N terminus of TLR9 has at least one of the following amino acid sequences:
  (a) the amino acid sequence represented by SEQ ID NO: 1;
  (b) an amino acid sequence derived from the amino acid sequence represented by SEQ ID NO: 1 by the deletion, substitution or addition of one or more amino acids; and
  (c) an amino acid sequence having 90% or higher identity to the amino acid sequence represented by SEQ ID NO: 1.
[5] The antibody according to any of [1] to [4], wherein the antibody comprises at least one of the following amino acid sequences:
  (a) the amino acid sequence represented by SEQ ID NO: 2;
  (b) the amino acid sequence represented by SEQ ID NO: 4;
  (c) the amino acid sequence represented by SEQ ID NO: 6;
  (d) the amino acid sequence represented by SEQ ID NO: 8;
  (e) the amino acid sequence represented by SEQ ID NO: 10;
  (f) the amino acid sequence represented by SEQ ID NO: 12;
  (g) an amino acid sequence derived from the amino acid sequence represented by any of SEQ ID NOs: 2, 4, 6, 8, and 10 by the deletion, substitution or addition of one or more amino acids; and (h) an amino acid sequence having 90% or higher identity to the amino acid sequence represented by any of SEQ ID NOs: 2, 4, 6, 8, and 10.

[6] The antibody according to any of [1] to [5], wherein the N terminus of TLR9 is the N terminus of mouse TLR9.

[7] A pharmaceutical composition for use in the treatment or prevention of a disease related to TLR9, comprising an antibody according to any of [1] to [6].

[8] The pharmaceutical composition according to [7], wherein the disease related to TLR9 is systemic lupus erythematosus, psoriasis, or non-alcoholic steatohepatitis.

[9] A kit for use in the diagnosis of a disease related to TLR9, comprising an antibody according to any of [1] to [6].

Advantageous Effects of Invention

An antibody recognizing the N-terminal side of TLR9, even when administered with a TLR9 agonist CpG-B, inhibited a TLR9 response and suppressed the production of tumor necrosis factor (TNF)-α in bone marrow-derived macrophages (BM-MCs) in vitro.

Such a TLR9 response suppressive effect of this antibody was similarly confirmed in vivo. Specifically, it was found that individuals of mice given a TLR9 agonist (CpG-B) and D-galactosamine die due to hepatocyte apoptosis induced by TNFα produced from hepatocyte-derived macrophages, whereas the administration of the antibody significantly suppresses the production of cytokines such as TNFα or IL-12p40 in serum so that the death of mouse individuals is circumvented.

These results suggest that the antibody of the present invention is capable of controlling pathological conditions involving abnormal activation of TLR9. For example, SLE is thought to be induced partly because DNA accumulation ascribable to deficiency in DNase gene stimulates a DNA sensor and thereby causes production of type I IFN. The antibody of the present invention can control the DNA sensor TLR9 and is therefore probably usable in the treatment or prevention SLE.

Thus, the antibody according to the present invention is capable of preventing or treating a disease related to TLR9 by inhibiting the function of TLR9 present on cell surface. Also, the antibody according to the present invention has high specificity for TLR9 and is therefore excellent in safety.

BRIEF DESCRIPTION OF DRAWINGS

FIG. 8 shows results of analyzing an epitope for a NaR9 antibody by examining the binding of the NaR9 antibody to chimeric TLR9.

FIG. 9 shows the amino acid sequence (SEQ ID NO: 14) of the heavy chain of the NaR9 antibody.

FIG. 10 shows the nucleotide sequence (SEQ ID NO: 15) of the heavy chain of the NaR9 antibody.

FIG. 11 shows the amino acid sequence (SEQ ID NO: 16) of the light chain of the NaR9 antibody.

FIG. 12 shows the nucleotide sequence (SEQ ID NO: 17) of the light chain of the NaR9 antibody.

DESCRIPTION OF EMBODIMENTS

[Antibody]

Figure 1:
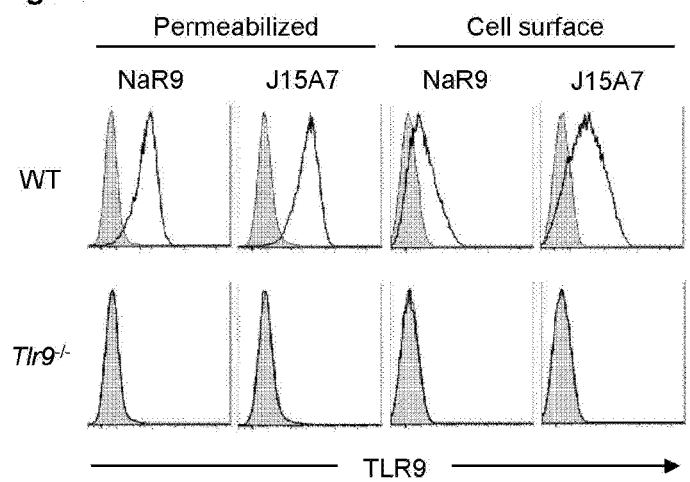
FIG. 1 shows results of an experiment revealing the expression of TLR9 using mouse spleen cDCs in order to verify the specificity of an antibody.

Mainly the C-terminal side of TLR9 has been thought to be important for exerting the function of TLR9. The antibody according to the present invention is capable of recognizing the N terminus of TLR9, particularly, an extracellular domain to be cleaved within endolysosome, and its neighborhood. Hereinafter, the antibody according to the present invention is also referred to as an "N terminus-recognizing antibody" or an "anti-TLR9 antibody".

In the present specification, the "N terminus of TLR9" means the first half region from the N terminus of TLR9 to position 440 or 454. The extracellular domain means a region at the N terminus of TLR9 from position 1 to position 818. The "C terminus of TLR9" means the region of TLR9 that is not the extracellular domain.

In the protein of TLR9, an amino acid unit with no amino group bonded and a carboxyl group bonded is defined as position 1, and subsequent amino acid units are referred to as positions 2, 3, etc. from the N terminus of TLR9 toward the C terminus of TLR9.

The N terminus-recognizing antibody recognizes, for example, a region from positions 1 to 166, 1 to 242, 1 to 306, 1 to 356, or 1 to 440, preferably a region from positions 1 to 356, more preferably a region from positions 167 to 356, further preferably a region from positions 243 to 356, at the N terminus of TLR9.

Specifically, the N terminus-recognizing antibody recognizes the N terminus of TLR9 which is at least one of the following amino acid sequences:

(a) the amino acid sequence represented by SEQ ID NO: 1;

(b) an amino acid sequence derived from the amino acid sequence represented by SEQ ID NO: 1 by the deletion, substitution or addition of one or more amino acids; and (c) an amino acid sequence having 80% or higher, preferably 90% or higher identity to the amino acid sequence represented by SEQ ID NO: 1.

The mouse TLR family is known to consist of 12 members, while the human TLR family is known to consist of 10 members. TLR1, TLR2, TLR4, TLR5, and TLR6 are distributed in the cell surface and recognize lipoproteins which are bacterial membrane components, glycolipids such as LPS, or proteins such as flagellin. TLR3, TLR7, TLR8, and TLR9 are distributed in endoplasmic reticula which are intracellular organelles and recognize bacterium- or virus-derived nucleic acids. TLR is a type I membrane protein extracellularly having leucine-rich repeat (LRR).

Figure 7:
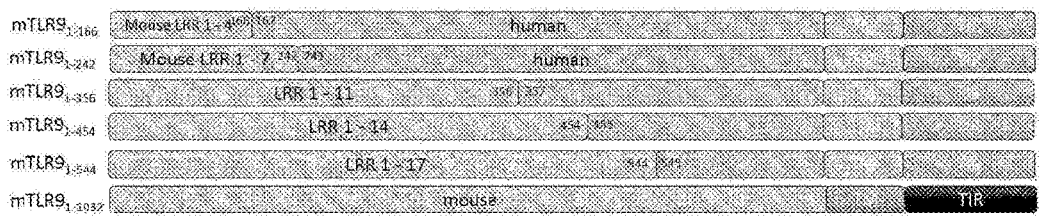
FIG. 7 shows chimeric TLR9 wherein the chimeric TLR9 was prepared from mouse TLR9 and human TLR9.

The N terminus-recognizing antibody recognizes the N terminus of mouse TLR9, human TLR9, or mouse/human chimeric TLR9 and is not particularly limited as long as the antibody recognizes the N terminus of TLR9. The N terminus of TLR9 that is recognized by the N terminus-recognizing antibody is, for example, the N terminus of mouse/human chimeric TLR9 shown in FIG. 7.

The N terminus-recognizing antibody is not particularly limited as long as the antibody recognizes the N terminus of TLR9. The N terminus-recognizing antibody comprises, for example, at least one of the following amino acid sequences:

(a) the amino acid sequence represented by SEQ ID NO: 2;

(b) the amino acid sequence represented by SEQ ID NO: 4;

(c) the amino acid sequence represented by SEQ ID NO: 6;

(d) the amino acid sequence represented by SEQ ID NO: 8;

(e) the amino acid sequence represented by SEQ ID NO: 10;

(f) the amino acid sequence represented by SEQ ID NO: 12;

(g) an amino acid sequence derived from the amino acid sequence represented by any of SEQ ID NOs: 2, 4, 6, 8, 10, and 12 by the deletion, substitution or addition of one or more amino acids; and (h) an amino acid sequence having 80% or higher, preferably 90% or higher identity to the amino acid sequence represented by any of SEQ ID NOs: 2, 4, 6, 8, 10, and 12.

The N terminus-recognizing antibody may comprise at least one of heavy chain CDR1 to CDR3 and light chain CDR1 to CDR3, preferably at least one of heavy chain CDR1 to CDR3, more preferably heavy chain CDR3, with the amino acid sequences (a) to (c).

In the present specification, the "amino acid" is used in its broadest sense and is meant to include not only a natural amino acid but also a non-natural amino acid such as amino acid variant or derivative. Examples of the amino acid include, but are not limited to: natural proteinaceous L-amino acids; D-amino acids; chemically modified amino acids such as amino acid variants and derivatives; natural nonproteinaceous amino acids such as norleucine, β-alanine, and ornithine; and chemically synthesized compounds having properties characteristic to amino acids and known in the art. Examples of the non-natural amino acids include, but not limited to, α-methylamino acids (α-methylalanine, etc.), D-amino acids, histidine-like amino acids (2-amino-histidine, β-hydroxy-histidine, homohistidine, α-fluoromethyl-histidine, α-methyl-histidine, etc.), amino acids having, in the side chain thereof, excess methylene ("homo" amino acids, etc.), and amino acids derived from an amino acid having a carboxylic acid functional group in the side chain thereof by the substitution of the group by a sulfonic acid group (cysteic acid, etc.).

In the present specification, the number of amino acids to be deleted, substituted, or the like in the phrase "derived by the deletion, substitution or addition of one or more amino acids" is not particularly limited as long as the resulting set of CDRs retains the function of recognizing the antigen. In this context, the term "more" means an integer of 2 or larger, preferably several, for example, 2 to 5, more preferably 2, 3, or 4. The position of deletion, substitution, or addition in each CDR may be the N terminus, the C terminus, or between the N and C termini as long as the resulting set of CDRs retains the function of recognizing the antigen.

In the present specification, the phrase "having Y % or higher identity to the amino acid sequence represented by SEQ ID NO: X" means that when two polypeptides are arranged (aligned) to give the maximum coincidence of their amino acid sequences, the proportion of the number of amino acid residues in common is Y % or higher based on the total number of amino acids shown in SEQ ID NO: X.

The N terminus-recognizing antibody may be a monoclonal antibody or may be a polyclonal antibody. Also, the N terminus-recognizing antibody may be of any of isotypes IgG, IgM, IgA, IgD and IgE.

The N terminus-recognizing antibody may be a mouse antibody, a human CDR-grafted antibody, a human chimeric antibody, a humanized antibody, or a fully human antibody or may be a low-molecular antibody as long as the antibody binds to TLR9 on the cell surface and inhibits its function, though the N terminus-recognizing antibody is not limited thereto.

The human CDR-grafted antibody is an antibody obtained by substituting CDRs of a non-human animal antibody with CDRs of a human antibody. The human chimeric antibody is an antibody composed of variable regions derived from a non-human animal antibody and constant regions derived from a human antibody. The humanized antibody is an antibody obtained by incorporating a moiety derived from a human antibody into a non-human animal antibody while leaving a highly safe partial region of the non-human animal antibody, and conceptually includes the human chimeric antibody and the human CDR-grafted antibody.

In the present specification, the "low-molecular antibody" means an antibody fragment or an antibody fragment bound with an arbitrary molecule that recognizes the same epitope as that recognized by the original antibody. Specific examples thereof include, but are not limited to: Fab composed of VL, VH, CL, and CH1 regions; F(ab')2 in which two Fabs are linked to each other via a disulfide bond in the hinge region; Fv composed of VL and VH; and scFv which is a single-chain antibody in which VL and VH are linked to each other via an artificial polypeptide linker, and additionally include sdFv, Diabody, and sc(Fv)2.

[Method for Preparing Antibody]

The method for preparing the N terminus-recognizing antibody is not limited. For example, a monoclonal antibody can be obtained by isolating antibody-producing cells from a non-human mammal immunized with TLR9 or a fragment thereof, fusing these cells with myeloma cells or the like to prepare hybridomas, and purifying an antibody produced by these hybridomas. Also, a polyclonal antibody can be obtained from the serum of an animal immunized with TLR9 or a fragment thereof. The fragment of TLR9 for use in immunization is not particularly limited as long as the resulting antibody binds to TLR9 on the cell surface and inhibits its function.

In the case of preparing an antibody having a particular amino acid sequence, the antibody can be prepared, for example, by transforming an appropriate host with an expression vector containing a nucleic acid encoding the antibody, culturing the transformant under appropriate conditions to express an antibody, and isolating and purifying the antibody according to a known method. Examples of the isolation and purification method include affinity column using protein A or the like, other chromatography columns, filters, ultrafiltration, salting-out, and dialysis. These methods can be appropriately combined.

The "antibody Y specifically binding to the same epitope as that for certain antibody X" can be prepared after determination of the sequence of the epitope as described below.

For example, an epitope on an antigen protein can be determined by immobilizing many peptides having a random sequence to a solid-phase carrier to form an array, reacting the array with the antibody X, detecting binding using an enzymatically labeled secondary antibody, examining the amino acid sequence of the peptide to which the antibody X specifically binds, and retrieving homology between this amino acid sequence and the amino acid sequence of the antigen protein. The peptides to be immobilized onto a solid-phase carrier may be a group of partial peptides of the antigen protein prepared in advance. Alternatively, an epitope on an antigen protein may be determined by detecting the binding between the antibody X and the antigen protein in the presence of various partial peptides of the antigen protein by ELISA, and examining the presence or absence of competitive activity.

Once the sequence of the epitope can be determined, antibody Y specifically binding to this epitope can be prepared by those skilled in the art according to a known method. For example, an antibody specifically binding to the epitope can be obtained by immobilizing a peptide containing the epitope sequence to a solid-phase carrier, and detecting the binding between the peptide and various antibodies.

In this context, antibodies obtained by immunizing animals with an antigen protein or a partial peptide thereof may be used as the "various antibodies", or an antibody library or an antibody fragment library prepared by a phage display method may be used there as. In the case of using a library prepared by a phage display method, antibody Y specifically binding to the epitope can also be obtained by immobilizing a peptide containing the epitope sequence onto a solid-phase carrier, and repeating panning.

A human chimeric antibody and a human CDR-grafted antibody can be prepared by cloning an antibody gene from the mRNA of a hybridoma producing a non-human animal antibody, and linking this gene with a portion of a human antibody gene through a gene recombination technique.

In the case of, for example, a human chimeric antibody, cDNA is synthesized from the mRNA of a hybridoma producing a mouse antibody, using reverse transcriptase. Heavy chain variable region (VH) and light chain variable region (LH) genes are cloned by PCR and analyzed for their sequences. Next, a 5' primer containing a leader sequence is prepared from an antibody nucleotide sequence having a high coincidence ratio, and a region from a signal sequence to the 3' end of each variable region gene is cloned from the cDNA by PCR using the 5' primer and a variable region 3' primer. Meanwhile, human IgG1 heavy chain and light chain constant region genes are cloned. For each of the heavy chain and the light chain, the mouse antibody-derived variable region gene and the human antibody-derived constant region gene are linked to each other and amplified by an overlapping hanging method based on PCR. The DNA thus obtained can be inserted into an appropriate vector, followed by transformation to obtain a human chimeric antibody.

In the case of a CDR-grafted antibody, human antibody variable regions having the highest homology to the mouse antibody variable regions used are selected, and their genes are cloned. The nucleotide sequences of CDRs are engineered by site-directed mutagenesis using a mega primer method. If the humanization of amino acid sequences constituting framework regions hinders the specific binding to an antigen, some amino acids of the frameworks may be converted from a human type to a rat type.

CDR consisting of the "amino acid sequence derived from the amino acid sequence represented by SEQ ID NO: X by the deletion, substitution or addition of one or more amino acids" or CDR consisting of the "amino acid sequence having Y % or higher identity to the amino acid sequence represented by SEQ ID NO: X" can be prepared by use of a known method such as site-directed mutagenesis, random mutagenesis, chain shuffling, or CDR walking.

It is well known to those skilled in the art that CDRs having more mature affinity can be obtained by displaying antibodies or antibody fragments having various mutations in their CDRs on the surface of phages by a phage display method according to these methods, and screening the antibodies or the antibody fragments using an antigen (e.g., Wu et al., PNAS, 95: 6037-6042 (1998); Schier, R. et al., J. Mol. Bio. 263: 551-567 (1996); Schier, R. et al., J. Mol. Biol. 255: 28-43 (1996); and Yang, W. P. et al., J. Mol. Biol., 254: 392-403 (1995)). The present invention also encompasses an antibody containing CDRs matured by such a method.

Other examples of the method for producing the antibody include the Adlib method (Seo, H. et al., Nat. Biotechnol., 6: 731-736, 2002) of obtaining an antibody-producing line from a DT40 cell line derived from trichostatin A-treated chicken B cells, and a method of immunizing KM mice, which are mice having a human antibody gene introduced therein instead of a disrupted mouse antibody gene, to prepare a human antibody (Itoh, K. et al., Jpn. J. Cancer Res., 92: 1313-1321, 2001; and Koide, A. et al., J. Mol. Biol., 284: 1141-1151, 1998). These methods can also be applied to the production of the N terminus-recognizing antibody.

When the N terminus-recognizing antibody is a low-molecular antibody, the antibody may be expressed by the above-described method while using DNA encoding this low-molecular antibody, or may be prepared by treating a full-length antibody with an enzyme such as papain or pepsin.

The N terminus-recognizing antibody may differ in amino acid sequence, molecular weight, isoelectric point, presence or absence of sugar chain, morphology, or the like depending on a preparation method or a purification method. However, the obtained antibody is included in the scope of the present invention as long as the antibody has a function equivalent to that of the N terminus-recognizing antibody. For example, when the N terminus-recognizing antibody is expressed in prokaryotic cells such as *E. coli*, a methionine residue is added to the N terminus of the amino acid sequence of the original antibody. Such an antibody is also included in the scope of the present invention.

[Pharmaceutical Composition]

The pharmaceutical composition according to the present invention comprises the N terminus-recognizing antibody and is used in the treatment or prevention of a disease related to TLR9.

Those skilled in the art can appropriately determine whether or not an antibody can be used in the treatment or prevention of a disease related to TLR9. For example, usability in the treatment or prevention of a disease related to TLR9 can be determined by confirming, according to a method shown in Example, at least one of (i) whether or not the obtained antibody binds to TLR9 on the cell surface; (ii) whether or not the amount of an inflammatory cytokine secreted from immune cells is reduced when the immune cells are brought into contact with the obtained antibody while stimulated with a TLR9 ligand; (iii) whether or not the proliferation of B cells is suppressed when the B cells are brought into contact with the obtained antibody while stimulated with a TLR9 ligand; and (iv) whether or not pathological conditions are ameliorated by administering the obtained antibody to an inflammatory disease animal model.

Examples of the disease related to TLR9 include various autoimmune diseases (rheumatoid arthritis (RA), systemic lupus erythematosus (SLE), scleroderma, polymyositis, Sjogren's syndrome (SS), ANCA-associated vasculitis, Behcet's disease, Kawasaki disease, mixed cryoglobulinemia, multiple sclerosis (MS), Guillain-Barre syndrome, myasthenia, type 1 diabetes, Graves' disease, Hashimoto's disease, Addison's disease, IPEX, APS type-II, autoimmune cardiomyopathy, interstitial pneumonia, bronchial asthma, autoimmune hepatitis, non-alcoholic steatohepatitis (NASH), primary biliary cirrhosis, inflammatory bowel disease (IBD), Crohn's disease, ulcerative colitis, psoriasis, atopic dermatitis, hemolytic anemia, autoimmune thyroiditis, and polyarticular juvenile idiopathic arthritis, etc.), graft rejection, and graft versus host disease (GvHD).

The pharmaceutical composition is potentially useful for, among these diseases, SLE, psoriasis, or NASH which develops under a mechanism involving TLR9. While not intending to be bound by any theory, for example, the N terminus-recognizing antibody is thought to contribute to the treatment or prevention of psoriasis related to TLR9 by recognizing TLR9 on the cell surface and inhibiting a TLR9 response of the cells, thereby suppressing the abnormal activation of immunity.

A steroid drug such as prednisolone has heretofore been used for, for example, SLE or its related disease systemic sclerosis. Also, belimumab, an antibody against B lymphocyte stimulator (Blys) involved in the activation of B cells, is used as a biological formulation. However, all of these drugs involve resistant cases. Thus, there is a demand for a therapeutic drug targeting a novel molecule for such diseases.

In SLE, type I interferon (IFN) is excessively produced. Cells producing type I IFN are pDCs (plasmacytoid dendritic cells), and the production is induced by DNA stimulation. The N terminus-recognizing antibody can therapeutically target TLR9 as a DNA sensor expressed on pDCs and is therefore useful in the treatment or prevention of SLE.

The pharmaceutical composition according to the present invention comprises the N terminus-recognizing antibody as an active ingredient and further contains a pharmaceutically acceptable carrier or additive.

Examples of the carrier and the additive include, but are not limited to, water, saline, pharmaceutically acceptable organic solvents such as phosphate buffers, dextrose, glycerol, and ethanol, collagen, polyvinyl alcohol, polyvinylpyrrolidone, carboxyvinyl polymers, sodium carboxymethylcellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, Vaseline, paraffin, stearyl alcohol, stearic acid, human serum albumin, mannitol, sorbitol, lactose, and surfactants.

The pharmaceutical composition according to the present invention can be provided in various forms, for example, solutions (e.g., injections), dispersions, suspensions, tablets, pills, powders, or suppositories. A preferred form is an injection, which is preferably administered parenterally (e.g., intravenously, transdermally, intraperitoneally, or intramuscularly).

In the present specification, the "treatment or prevention" means causing at least one of recovery and remission of a disease, prevention or retardation of onset, prevention and retardation of the progression of a disease, and relief of at least one of the symptoms associated with a disease.

In the case of administering the pharmaceutical composition according to the present invention to mammals (e.g., humans, mice, rats, guinea pigs, rabbits, dogs, horses, monkeys, and pigs), particularly, to humans, the dose differs depending on symptoms, the age, sex, weight, and sensitivity difference of a patient, an administration route, an administration interval, the type of the active ingredient, and the type of a formulation and is not particularly limited. For example, a dose from 30 µg to 1000 mg, from 100 µg to 500 mg, or from 100 µg to 100 mg can be administered once or in several portions. For administration through injection, a dose from 1 µg/kg to 5000 µg/kg or from 3 µg/kg to 3000 µg/kg may be administered once or in several portions based on the weight of a patient.

(Kit)

The kit according to the present invention comprises the N terminus-recognizing antibody. The purpose of the kit is not particularly limited, and the kit is used in the detection of TLR9 or the diagnosis of a disease related to TLR9.

The kit may contain a reagent, or a carrier or an additive, as in the pharmaceutical composition, according to the purpose, and may further contain a buffer, a container, an instruction manual, and the like.

(Method)

The method according to the present invention comprises the step of administering the N terminus-recognizing antibody to a subject.

In the method according to the present invention, the N terminus-recognizing antibody can be administered as the pharmaceutical composition according to the present invention.

The method according to the present invention can treat or prevent a disease related to TLR9 in a human or any of other mammals, etc., which is a subject. Alternatively, the method of the present invention may be used for other purposes, for example, diagnosis.

The disclosure of all patent literatures and non patent literatures cited herein is incorporated herein by reference in its entirety.

EXAMPLES

Hereinafter, the present invention will be described specifically with reference to Examples. However, the present invention is not limited by these examples by any means. Those skilled in the art can change the present invention into various modes without departing from the principle of the present invention, and such a change is also included in the scope of the present invention.

Establishment of anti-TLR9 antibody, detection of TLR9 in primary immune cell, and TLR9 response inhibition test of anti-TLR9 antibody

[Material and Method]

Preparation of Anti-TLR9 Monoclonal Antibody NaR9

In order to establish an anti-mouse TLR9 monoclonal antibody, a Tlr9$^{-/-}$ mouse of BALB/c background was immunized by the intraperitoneal administration of Ba/F3 cells forced to express mouse TLR9 (TLR9-Ba/F3). The initial immunization employed complete Freund's adjuvant (CFA) as an immunostimulator. The second and third immunizations employed incomplete Freund's adjuvant (IFA) as an immunostimulator. For the fourth immunization, TLR9-Ba/F3 suspended in 1 (PBS (phosphate-buffered saline) was intraperitoneally administered to the mouse. Five days after the final immunization, the spleen cells of the mouse were fused with a mouse myeloma-derived cell line SP2/0. The cell fusion employed hemagglutinating virus of Japan-derived envelope protein (GenomeONE-CF) purchased from Ishihara Sangyo Kaisha, Ltd. In order to select a hybridoma producing an antibody against TLR9, cell membrane permeability staining was performed using TLR9-Ba/F3, followed by analysis by flow cytometry. The subclass of NaR9 was determined as IgG2a/κ using Mouse antibody Isotype kit purchased from Bio-Rad Laboratories, Inc.

Mouse

Wild-Type C57BL/6 Mice were Purchased from Japan SLC, Inc.

TLR9-deficient mice (Tlr9$^{-/-}$) of C57BL/6 background were established in our laboratory. Tlr9$^{-/-}$ mice of BALB/c background were established by mating seven times with the wild-type BALB/c mice purchased from Japan SLC, Inc. The mice were raised in an SPF environment, and all animal experiments were conducted under the approval of the animal experiment committee of the Institute of Medical Science, The University of Tokyo.

Reagent and Antibody

CpGA 1585 (5'-G*G*GGTCAACGTTGAG*G*G*G*G-3'; the asterisk represents a phosphorothioation residue) (SEQ ID NO: 19), PolyU (5'-UUUUUUUUUUUUUUUUUUUU-3'; all are phosphorothioation residues) (SEQ ID NO: 20) and CpGB 1688 (5'-TCCATGACGTTCCTGATGCT-3'; all are phosphorothioation residues) (SEQ ID NO: 18) were synthesized by FASMAC. Loxoribine (7-allyl-7,8-dihydro-8-oxo-guanosine) was purchased from Enzo Life Sciences, Inc. Saponin and D-(+)-galactosamine were purchased from Sigma-Aldrich Co. LLC. FuGene6 and DOTAP were purchased from Roche Applied Science. Anti-mouse TLR9 monoclonal antibodies NaR9, J15A7 and B33A4 were purified from the ascitic fluids of nude mice (purchased from Oriental Yeast Co., Ltd.) inoculated with hybridomas. Streptavidin-PE, anti-mouse IgG1-PE, anti-mouse IgG2a-PE, isotype control antibodies (mouse IgG1 and mouse IgG2a), anti-mouse CD16/32, anti-mouse CD19-APC-Cy7, anti-mouse CD11b-APC, anti-mouse CD11c-APC, anti-mouse CD11c-PE-Cy7, anti-mouse Siglec-H-FITC, and anti-mouse Ly-6G-PerCP-Cy5.5 were purchased from BioLegend, Inc. Anti-mouse B220-APC was purchased from TONBO Biosciences Inc. J15A7-PE, anti-mouse CD49b-BV421 and anti-mouse CD11b-BV510 were purchased from BD Biosciences.

Cell Culture

Ba/F3 cells were cultured in Roswell Park Memorial Institute (RPMI) 1640 medium (supplemented with IL-3, 10% FBS, PS/Gln and 50 μM 2-ME). Bone marrow-derived macrophages (BM-MCs), conventional DCs (cDCs) or plasmacytoid DCs (pDCs) were induced from wild-type C57BL/6 mice or Tlr9$^{-/-}$ mice. In order to induce the macrophages, 1×10$^7$ bone marrow cells were cultured for 6 days in 10% FCS-RPMI1640 supplemented with 100 ng/ml recombinant M-CSF (PeproTech, Rocky Hill, N.J., USA) in 10 cm cell culture dishes. In order to induce the cDCs or the pDCs, 1×10$^7$ bone marrow cells were cultured for 7 days in 10% FCS-RPMI1640 supplemented with 10 ng/ml recombinant GM-CSF or 100 ng/ml Flt3-L (PeproTech, Rocky Hill, N.J., USA) in 10 cm cell culture dishes.

Construction of Plasmid and Transfection Using Retrovirus Vector

The gene sequence of mouse or human TLR9 was amplified by PCR and cloned into a pMX or pMXs retrovirus vector kindly given by Prof. Toshio Kitamura from the University of Tokyo. Mouse/human TLR9 chimeric variants describe below were constructed. The genes of TLR9$_{166}$ (mouse TLR9 amino acids from positions 1 to 166 and human TLR9 amino acids from positions 167 to 1016), TLR9$_{242}$ (mouse TLR9 amino acids from positions 1 to 242 and human TLR9 amino acids from positions 243 to 1016), =$^9$$_{356}$ (mouse TLR9 amino acids from positions 1 to 356 and human TLR9 amino acids from positions 357 to 1016), TLR9$_{440}$ (mouse TLR9 amino acids from positions 1 to 440 and human TLR9 amino acids from positions 441 to 1016) and TLR9$_{544}$ (mouse TLR9 amino acids from positions 1 to 544 and human TLR9 amino acids from positions 545 to 1016) were each cloned into a pMX-GFP vector so as to add GFP to the C-terminal side of each TLR9 variant.

Plat-E packaging cells (1×10$^3$ cells/well) were transfected with each plasmid together with polyethylenimine (Polysciences, Inc.). Two days later, a culture supernatant containing viruses was added together with DOTAP to Ba/F3 cells, which were then centrifuged at 2000 rpm for 60 minutes.

Staining of Spleen Immune Cell and Flow Cytometry Analysis

The spleen was collected from each of wild-type mice and TLR9-knockout mice of C57BL/6N lineage, and cells were isolated using glass slides. The isolated cells were treated with an erythrolysis buffer (BioLegend, Inc.) to remove erythrocytes. Then, Fc receptor on the cell surface was blocked using purified anti-CD16/32 (BioLegend, Inc., clone 93).

After the blocking of the Fc receptor, the resultant was stained with Fluorescein (FITC)-conjugated anti-mouse SiglecH (BioLegend, Inc., 551) and Phycoerythrin (PE)-Cy7-conjugated anti-mouse CD11c (BioLegend, Inc., N418). A CD11c-positive/SiglecH-positive fraction was regarded as pDCs. A highly CD11c expressing/SiglecH-negative fraction was regarded as cDCs.

After the staining of SiglecH and CD11c on the cell surface, TLR9 on the cell surface and inside the cells was stained. In order to stain TLR9 on the cell surface, the cell surface was reacted with purified anti-TLR9 under nonfixed conditions, and PE conjugated rat anti-mouse IgG2a (BioLegend, Inc., clone RMG2a-62) was used as a secondary antibody. TLR9 inside the cells was stained using BD Cytofix/Cytoperm fixation/permeabilization solution kit. These cells were buffer-replaced with a buffer for staining and analyzed using LSRFortessa X-20 (BD).

Immunoprecipitation and Western Blot

The protein expression of TLR9 was analyzed by Western blot. BM-cDCs were washed twice with 1×PBS and recovered. The recovered cells were lysed for 30 minutes in an ice-cold buffer for lysis (1% Triton X 100, 20 mM Tris-HCl (pH 7.4), 150 mM NaCl, 1 mM CaCl$_2$, 1 mM MgCl$_2$, 10% glycerol, 1 mM DTT and Complete protease Inhibitor Cocktail (F. Hoffmann-La Roche, Ltd.)) and centrifuged at a high speed, followed by the recovery of the supernatant of the cell lysate.

The recovered cell lysate was added to N-hydroxy succinimide-activated Sepharose 4FF beads bound with the anti-TLR9 monoclonal antibody (NaR9), and the mixture was stirred at 4° C. for 2 hours. TLR9 was immunoprecipitated by this step. The beads thus stirred were washed three times with an ice-cold buffer for washing (0.1% Triton X 100, 20 mM Tris/HCl (pH 7.4), 150 mM NaCl, 1 mM CaCl$_2$), 1 mM MgCl2, 0.1% glycerol, and 1 mM DTT). To the washed beads, an SDS sample buffer (125 mM Tris/HCl [pH 6.8], 20% glycerol, 4% SDS, 10% 2-ME, and 0.005% bromophenol blue) was added, and the mixture was heated at 96° C. for 5 minutes for protein denaturation treatment. The sample thus prepared was subjected to polyacrylamide electrophoresis, and the protein was transferred to a PVDF membrane and Western-blotted.

The antibody used in the Western blot was an autologous polyclonal antibody purified from serum recovered from a rabbit immunized with the TIR domain of mouse TLR9.

Statistical Processing

In an experiment of administering an antibody to mice, a significant difference test of data between an anti-TLR9 monoclonal antibody administration group and a control antibody administration group was conducted according to Student's t-test. A significance level of less than 0.01 in the t test was judged as being the significant difference between the compared groups.

TLR9 response inhibition experiment using anti-TLR9 monoclonal antibody (In Vitro Test)

The cells used were BM-MCs, BM-cDCs, and BM-pDCs. Each well of a 96-well flat-bottomed plate was inoculated with 5($10^4$ BM-MCs, BM-cDCs, or BM-pDCs, and an anti-TLR9 antibody was added thereto at each concentration. Four hours after the addition of the antibody, a TLR ligand was added to the inoculated cultured cells. Twenty-four hours after the addition of the TLR ligand, the culture supernatant was recovered. The recovered culture supernatant was subjected to ELISA to measure a cytokine produced by the stimulation with the ligand.

(In Vivo Test)

It has been reported that wild-type mice die within 10 hours by the intraperitoneal administration of a CpGB ligand and D-(+)-galactosamine at the same time (Sparwasser, T. et al., Eur J Immunol 27, 1671-1679, doi:10.1002/eji.1830270712 (1997)). An antibody or PBS (phosphate-buffered saline) was intraperitoneally administered to wild-type C57BL/6 mice. Fifteen hours later, 10 nmol of CpGB and 20 mg of D-(+)-galactosamine were further intraperitoneally administered to each mouse. Blood was collected from each mouse before the ligand administration and 1, 3, and 6 hours after the administration, and TNF-α or IL-12p40 was measured by ELISA using the serum.

Analysis on Amino Acid Sequence and Nucleotide Sequence of Antibody and CDR

The amino acid sequence of NaR9, a monoclonal antibody against TLR9, was analyzed by GenScript. Total RNA was recovered from the hybridoma using TRIzol(R) Reagent manufactured by Ambion, Inc., and subjected to reverse transcription reaction into cDNA using PrimeScript(R) 1st Strand cDNA Synthesis Kit manufactured by Takara Bio Inc. From this cDNA, $V_H$ and $V_L$ gene fragments were amplified, and each fragment was cloned into a general vector for cloning. After transformation of E. coli, plasmids were recovered by colony PCR from at least 5 clones with a band of a correct size and analyzed for their sequences. The highest consensus sequences were determined as the sequences of the antibody by the sequence analysis. As for the determined sequences of the antibody, FIG. 9 shows the amino acid sequence (SEQ ID NO: 14) of the heavy chain of the NaR9 antibody, FIG. 10 shows the nucleotide sequence (SEQ ID NO: 15) of the heavy chain of the NaR9 antibody, FIG. 11 shows the amino acid sequence (SEQ ID NO: 16) of the light chain of the NaR9 antibody, and FIG. 12 shows the nucleotide sequence (SEQ ID NO: 17) of the light chain of the NaR9 antibody.

[Results]

Establishment of Anti-TLR9 Monoclonal Antibody and Detection of TLR9

In order to examine the intracellular expression of endogenous TLR9 in primary immune cells, a NaR9 antibody was established as a monoclonal antibody against mouse TLR9. In order to verify the specificity of the antibody, the expression of TLR9 was revealed using mouse spleen cDCs. The specificity of staining was confirmed by the absence of a stain of the spleen cDCs of TLR9 knockout mice (FIG. 1).

Figure 2:
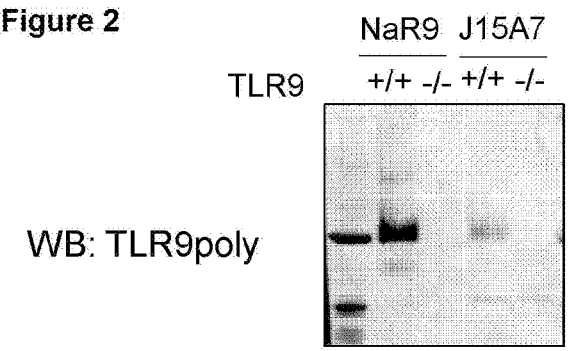
FIG. 2 shows results of conducting an immunoprecipitation experiment of TLR9 using spleen cDCs.
Figure 3:
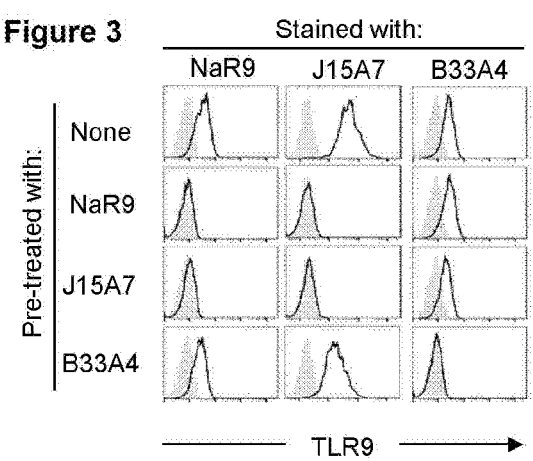
FIG. 3 shows results of conducting a staining inhibition experiment using an antibody against TLR9 (B33A4 and J15A7).

Further, the immunoprecipitation experiment of TLR9 was conducted using BM-cDCs. NaR9 was shown to more strongly immunoprecipitate TLR9 as compared with a previously established antibody against TLR9 (J15A7) (FIG. 2). In order to reveal the recognition site of NaR9, a staining inhibition experiment was first conducted using previously established antibodies against TLR9 (B33A4 and J15A7) (for B33A4 and J15A7, see International Publication No. WO 2014/174704). The TLR9 staining of NaR9 was inhibited by the pretreatment of cells with J15A7 (FIG. 3). Likewise, the TLR9 staining of J15A7 was inhibited by the pretreatment of cells with NaR9 (FIG. 3). These results demonstrated that the newly established NaR9 recognizes TLR9 on primary immune cells, can be utilized in cell staining or immunoprecipitation, and has an antigen recognition site similar to that of J15A7.

TLR9 Response Inhibition Test Using Anti-TLR9 Monoclonal Antibody—(1)

Figure 4:
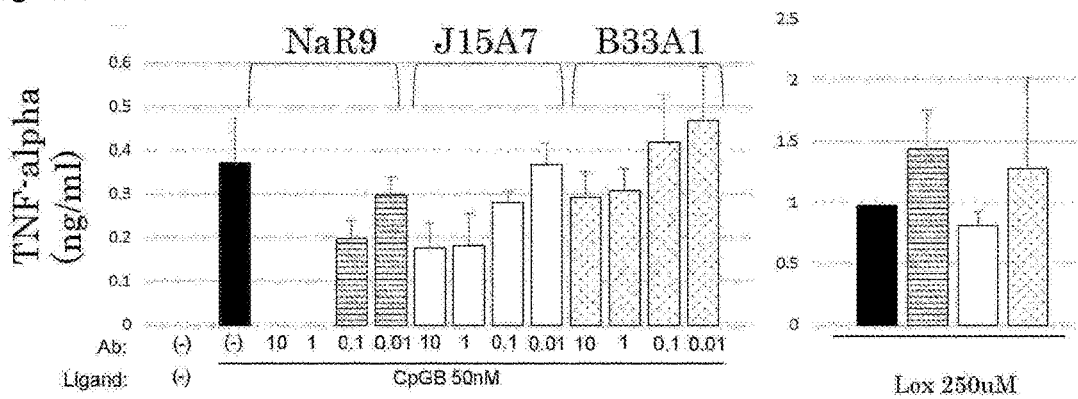
FIG. 4 shows results of an experiment of inducing BM-MCs from a wild-type mouse in order to verify the TLR9 response suppressive effect of NaR9.

In order to verify the TLR9 response suppressive effect of NaR9, BM-MCs were induced from wild-type mice and used in the experiment. In a NaR9 prior administration group, TNF-α and IL-12p40 production in BM-MCs in response to CpGB or CpGA was suppressed in an antibody concentration-dependent manner (FIG. 4). Similar results were obtained about BM-cDCs (data not shown). On the other hand, there was no influence on the loxoribine response of the TLR7 ligand. On the other hand, the TLR9 response suppressive effect of NaR9 was not observed in BM-pDCs (data not shown).

TLR9 Response Inhibition Test Using Anti-TLR9 Monoclonal Antibody—(2)

Figure 5:
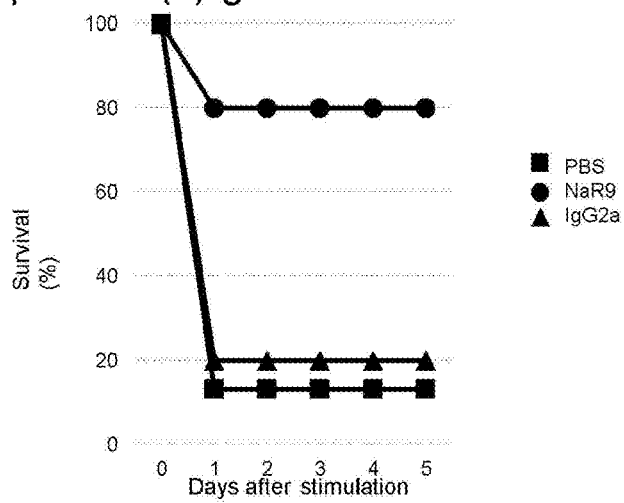
FIG. 5 shows results of conducting an experiment of administering CpGB and D-(+)-galactosamine to mice in order to verify the suppressive effect of NaR9 to TLR9 response in vivo.
Figure 6:
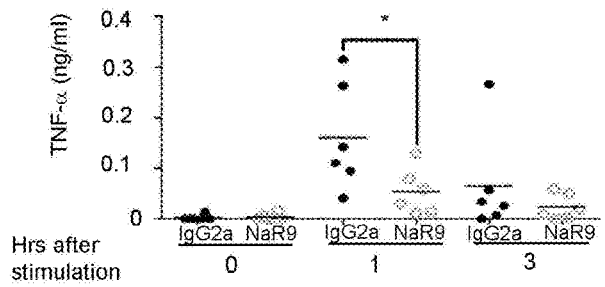
FIG. 6 shows results of measuring TNF-α in blood 1, 3, and 6 hours after ligands stimulation.

Subsequently, in order to verify the TLR9 response suppressive effect of NaR9 in vivo, an experiment of administering CpGB and D-(+)-galactosamine to a mouse was conducted. In a PBS or IgG2a control antibody prior administration group, approximately 90% of the mice died within 10 hours after ligand stimulation. By contrast, in a NaR9 prior administration group, the death rate was reduced to 20% (FIG. 5). As a result of further measuring TNF-α in blood 1, 3, and 6 hours after ligand stimulation, cytokine production was significantly suppressed in a NaR9 antibody administration group compared with an IgG2a control antibody administration group (FIG. 6).

Amino Acid Sequence Analysis of NaR9 Variable Regions

The heavy chain amino acid sequence of a monoclonal antibody obtained from the hybridoma line NaR9 is shown in SEQ ID NO: 14, and the light chain amino acid sequence thereof is shown in SEQ ID NO: 16. Nucleotide sequences corresponding to these amino acid sequences are shown in SEQ ID NOs: 15 and 17.

The amino acid sequences of the heavy chain CDR1 to CDR3 of this antibody are shown in SEQ ID NOs: 2, 4, and 6, and the amino acid sequences of light chain CDR1 to CDR3 are shown in SEQ ID NOs: 8, 10, and 12. Nucleotide sequences corresponding to these amino acid sequences are shown in SEQ ID NOs: 3, 5, 7, 9, 11, and 13.

Antigen Recognition Site Analysis of NaR9

In order to determine the antigen recognition site of NaR9, a cell line expressing chimeric TLR9 of mouse TLR9 and human TLR9 was prepared. The mouse TLR9 used was from amino acid positions 1 to 544 ($TLR9_{544}$), from amino acid positions 1 to 454 ($TLR9_{454}$), from amino acid positions 1 to 356 ($TLR9_{356}$), and from amino acid positions 1 to 242 ($TLR9_{242}$) of TLR9 shown in SEQ ID NO: 1, and the sequence of the human TLR9 was positioned on the C-terminal side to prepare each chimera (FIG. 7), which was then expressed in the cell line. The binding of NaR9 to each chimeric TLR9 was measured by flow cytometry.

The results are shown in FIG. 8. NaR9 did not bind to TLR9$_{242}$, but bound to TLR9$_{356}$, suggesting that an epitope for NaR9 is present in or near a region from positions 243 to 356 in the amino acid sequence of TLR9.

Free Text of Sequence Listing

SEQ ID NO: 1 represents the amino acid sequence of mouse TLR9.

SEQ ID NO: 2 represents the amino acid sequence of the heavy chain CDR1 of a NaR9 antibody.

SEQ ID NO: 3 represents the nucleotide sequence of the heavy chain CDR1 of the NaR9 antibody.

SEQ ID NO: 4 represents the amino acid sequence of the heavy chain CDR2 of the NaR9 antibody.

SEQ ID NO: 5 represents the nucleotide sequence of the heavy chain CDR2 of the NaR9 antibody.

SEQ ID NO: 6 represents the amino acid sequence of the heavy chain CDR3 of the NaR9 antibody.

SEQ ID NO: 7 represents the nucleotide sequence of the heavy chain CDR3 of the NaR9 antibody.

SEQ ID NO: 8 represents the amino acid sequence of the light chain CDR1 of the NaR9 antibody.

SEQ ID NO: 9 represents the nucleotide sequence of the light chain CDR1 of the NaR9 antibody.

SEQ ID NO: 10 represents the amino acid sequence of the light chain CDR2 of the NaR9 antibody.

SEQ ID NO: 11 represents the nucleotide sequence of the light chain CDR2 of the NaR9 antibody.

SEQ ID NO: 12 represents the amino acid sequence of the light chain CDR3 of the NaR9 antibody.

SEQ ID NO: 13 represents the nucleotide sequence of the light chain CDR3 of the NaR9 antibody.

SEQ ID NO: 14 represents the amino acid sequence of the heavy chain of the NaR9 antibody.

SEQ ID NO: 15 represents the nucleotide sequence of the heavy chain of the NaR9 antibody.

SEQ ID NO: 16 represents the amino acid sequence of the light chain of the NaR9 antibody.

SEQ ID NO: 17 represents the nucleotide sequence of the light chain of the NaR9 antibody.

SEQ ID NO: 18 represents the DNA sequence of CpGB.

SEQ ID NO: 19 represents the DNA sequence of CpGA.

SEQ ID NO: 20 represents the RNA sequence of PolyU.

The invention claimed is:

1. An antibody recognizing TLR9, said antibody comprising SEQ ID NO: 2, SEQ ID NO: 4, SEQ ID NO: 6, SEQ ID NO: 8, SEQ ID NO: 10, and SEQ ID NO: 12.

2. The antibody according to claim 1, wherein the antibody recognizes a region from positions 1 to 356 of TLR9.

3. The antibody according to claim 1, wherein the antibody recognizes a region from positions 243 to 356 of TLR9.

4. The antibody according to claim 1, wherein the TLR9 has at least one of the following amino acid sequences:
   (a) the amino acid sequence represented by SEQ ID NO: 1;
   (b) an amino acid sequence derived from the amino acid sequence represented by SEQ ID NO: 1 by the deletion, substitution or addition of one or more amino acids; and
   (c) an amino acid sequence having 90% or higher identity to the amino acid sequence represented by SEQ ID NO: 1.

5. The antibody according to claim 1, wherein the antibody comprises at least one of the following amino acid sequences:
   (a) the amino acid sequence represented by SEQ ID NO: 14;
   (b) the amino acid sequence represented by SEQ ID NO: 16; and
   (c) an amino acid sequence having 90% or higher identity to the amino acid sequence represented by SEQ ID NO: 14 or SEQ ID NO: 16.

6. The antibody according to claim 1, wherein the TLR9 is mouse TLR9.

7. A pharmaceutical composition comprising an antibody according to claim 1 and a pharmaceutically acceptable carrier or additive.

8. A kit comprising an antibody according to claim 1 packaged together with a reagent, a carrier, an additive, a buffer, or a container.

9. A method of inhibiting CpG-induced TNFα and/or IL-12p40 in a subject in need thereof, comprising the step of administering the antibody according to claim 1 to the subject.

10. The method according to claim 9, wherein the subject has a disease which is systemic lupus erythematosus, psoriasis, or non-alcoholic steatohepatitis.

11. The method according to claim 9, wherein the antibody recognizes a region from positions 1 to 356 of TLR9.

12. The method according to claim 9, wherein the antibody recognizes a region from positions 243 to 356 of TLR9.

13. The method according to claim 9, wherein the TLR9 has at least one of the following amino acid sequences:
(a) the amino acid sequence represented by SEQ ID NO: 1;
(b) an amino acid sequence derived from the amino acid sequence represented by SEQ ID NO: 1 by the deletion, substitution or addition of one or more amino acids; and
(c) an amino acid sequence having 90% or higher identity to the amino acid sequence represented by SEQ ID NO: 1.

14. The method according to claim 9, wherein the antibody comprises at least one of the following amino acid sequences:
(a) the amino acid sequence represented by SEQ ID NO: 14;
(b) the amino acid sequence represented by SEQ ID NO: 16; and
(c) an amino acid sequence having 90% or higher identity to the amino acid sequence represented by SEQ ID NO: 14 or SEQ ID NO: 16.

15. The method according to claim 9, wherein the TLR9 is mouse TLR9.

16. A method of inhibiting CpG-induced TNFα and/or IL-12p40 in a subject in need thereof, comprising
the step of administering the pharmaceutical composition according to claim 7 to the subject.

17. The method according to claim 16, wherein the subject has a disease which is systemic lupus erythematosus, psoriasis, or non-alcoholic steatohepatitis.

18. A method of inhibiting or reducing TLR9 activity in a subject, which comprises administering to the subject an antibody according to claim 1.

19. A method of inhibiting or reducing TLR9 activity in a subject, which comprises administering to the subject a pharmaceutical composition according to claim 7.

* * * * *